(12) United States Patent
Opitz et al.

(10) Patent No.: US 8,364,247 B2
(45) Date of Patent: Jan. 29, 2013

(54) METHODS FOR DETERMINING THE SEX OF BIRDS' EGGS

(75) Inventors: Joerg Opitz, Dresden (DE); Bjoern Fischer, Limbach-Oberfohna (DE); Petra Morgenstern, Dresden (DE); Juergen Schreiber, Dresden (DE); Carola Gerich, Dresden (DE)

(73) Assignee: Fraunhofer-Gesellschaft zur Foerderung der Angwandten Forschung E.V., Munich (DE)

( * ) Notice: Subject to any disclaimer, the term of this patent is extended or adjusted under 35 U.S.C. 154(b) by 156 days.

(21) Appl. No.: 12/960,678

(22) Filed: Dec. 6, 2010

(65) Prior Publication Data
US 2011/0144473 A1 Jun. 16, 2011

(30) Foreign Application Priority Data
Dec. 16, 2009 (EP) .................................... 09015586

(51) Int. Cl.
*A61B 6/00* (2006.01)
(52) U.S. Cl. ........ 600/477; 600/476; 600/475; 600/473; 600/478; 424/9.6; 356/326; 119/50.7; 119/6.8
(58) Field of Classification Search .................. 600/407, 600/473–477, 478; 424/9.1, 9.6; 850/31; 356/326; 119/50.7, 6.8
See application file for complete search history.

(56) References Cited

U.S. PATENT DOCUMENTS

| | | | |
|---|---|---|---|
| 5,648,468 A * | 7/1997 | Spaulding | 530/359 |
| 5,679,514 A * | 10/1997 | Baker | 435/6.11 |
| 6,029,080 A * | 2/2000 | Reynnells et al. | 600/407 |
| 6,365,339 B1 * | 4/2002 | Daum et al. | 435/4 |
| 6,396,938 B1 | 5/2002 | Tao et al. | |
| 6,506,570 B1 * | 1/2003 | Phelps | 435/7.21 |
| 6,512,839 B1 * | 1/2003 | Toelken | 382/110 |
| 6,535,277 B2 * | 3/2003 | Chalker et al. | 356/53 |
| 6,805,244 B1 * | 10/2004 | Toelken | 119/6.8 |
| 6,989,238 B2 * | 1/2006 | Phelps | 435/7.21 |
| 7,041,439 B2 * | 5/2006 | Phelps et al. | 435/4 |
| 7,167,579 B2 * | 1/2007 | Taniguchi | 382/110 |
| 7,481,179 B2 * | 1/2009 | Cantrell et al. | 119/6.8 |
| 7,950,349 B1 * | 5/2011 | Rollins | 119/6.8 |
| 2002/0157613 A1 | 10/2002 | Phelps et al. | |

(Continued)

FOREIGN PATENT DOCUMENTS

DE 697 11 943 T2 11/2002
DE 10 2007 013 107 A1 9/2008

(Continued)

*Primary Examiner* — Tse Chen
*Assistant Examiner* — Amanda Lauritzen
(74) *Attorney, Agent, or Firm* — Marshall & Melhorn, LLC

(57) ABSTRACT

The invention relates to methods for determining the sex of birds' eggs. It can be used for an early determination of the sex, in particular in poultry farming, and in this respect also with non-incubated eggs. In the method in accordance with the invention, electromagnetic radiation is emitted onto the blastodisk of an egg by a radiation source and, after a switching off of the radiation source, the decay behavior of the autofluorescence intensity excited by the electromagnetic radiation is detected by a detector at the irradiated region of the blastodisk with time resolution and spectral resolution for at least one wavelength of the autofluorescence. The fractal dimension $D_F$ is calculated using the determined measured intensity values and the value of the fractal dimension $D_F$ is compared with a species-specific and sex-specific limit value, wherein, when the limit value is exceeded, the respective egg is classified as female and, when it is not reached, the egg is classified as male.

9 Claims, 5 Drawing Sheets

| U.S. PATENT DOCUMENTS | | | |
|---|---|---|---|
| 2006/0160080 A1* | 7/2006 | Clinton | 435/6 |
| 2008/0097174 A1 | 4/2008 | Maynard et al. | |
| 2012/0058052 A1* | 3/2012 | Decuypere et al. | 424/9.6 |
| 2012/0084873 A1* | 4/2012 | Sinclair et al. | 800/19 |

| FOREIGN PATENT DOCUMENTS | | |
|---|---|---|
| WO | 2008050335 A2 | 5/2008 |
| WO | 2008093336 A2 | 8/2008 |

* cited by examiner

METHODS FOR DETERMINING THE SEX OF BIRDS' EGGS

BACKGROUND OF THE INVENTION

The invention relates to methods for determining the sex of birds' eggs. It can be used for an early determination of the sex, in particular in poultry farming.

Eggs are normally incubated after laying, which predominantly takes place in incubators which have to be heated for several days or weeks in accordance with the type of bird. However, since breeding is carried out in a sex-specific manner, a sex determination after hatching is required. This can be done manually, which naturally represents a high effort and/or expense.

The hatched chicks having the respective unwanted sex are predominantly destroyed in this process, which is contrary to the interests of animal protection.

Different possibilities have been tried for this reason to be able to carry out a sex determination with sufficient accuracy in as early a stage as possible.

It is thus proposed in DE 10 2007 013 107 A1 to examine DNA-relevant cell material with light and in this process to measure molecule oscillation spectra which are to be compared with reference spectra. This is to take place by means of Raman spectroscopy, IR spectroscopy or terahertz spectroscopy. The results thus obtained have a very high error rate, in particular on a measurement within an egg, since all the contents contained in an egg exert an influence during this process. High intensities are required for the irradiation which result in a heating and consequently in an impairment of the irradiated cells. The accuracy can only be increased in these procedures in that eggs are examined which have already been incubated for several days.

This likewise relates to the method described in DE 697 11 943 T2. In this respect, the content of a sex-specific hormone contained in extraembryonic liquid should be determined.

SUMMARY OF THE INVENTION

It is therefore the object of the invention to be able to carry out the determination of the sex of birds on eggs with an increased accuracy and with little effort and/or expense.

This object is achieved in accordance with the invention by a method having the features of claim 1. Advantageous embodiments and further developments of the invention can be achieved with features denoted in dependent claims.

In the method in accordance with the invention, electromagnetic radiation is emitted onto the blastodisk of an egg using a radiation source. In this process, autofluorescence can be excited at the irradiated region of the blastodisk by the electromagnetic radiation used. After a switching off of the radiation source, the decay behavior of the autofluorescence intensity excited by the electromagnetic radiation is detected using a detector at the irradiated region of the blastodisk in a time-resolved and spectrum-resolved manner for at least one wavelength of the autofluorescence.

The fractal dimension $D_F$ can then be calculated using the determined measured intensity values and the value of the fractal dimension $D_F$ is then compared with a species-specific and sex-specific limit value. If the limit value is exceeded, the respective egg is then classified as female and if it is not reached, the egg is classified as male. The determination security of the respective sex can be increased in that a limit value is taken into account in the invention which not only takes the respective bird species into account, but also the respective breed.

After the radiation source for the electromagnetic radiation to excite the autofluorescence has been switched off, the intensity of the autofluorescence decreases over time. A relaxation into the base state after the switching off of the radiation source can be assumed.

A non-exponential decay can generally be observed in fractal structures which can be described by the following equations:

$$I(t) \approx t^{-\alpha} \qquad (1)$$

$$D_F = 2 - \frac{\alpha}{2} \qquad (2)$$

Two different possibilities for describing the fractal dimension $D_F$ can be used. In this respect, the determination of the maximum of the function may be of significance and be taken into account. Specific further wavelengths which are larger or smaller than the maximum can preferably also be included in the calculations. These selected wavelengths can differ from one another with a constant difference so that an interval of 1.5 nm between adjacent wavelengths can be observed.

The detected time-resolved fluorescence spectra are evaluated with the aid of fractal analysis. Different molecules can be excited simultaneously by an excitation of autofluorescence with suitable radiation and said molecules can mutually influence one another by electronic, photonic and oscillation states. In addition, in this respect, saturation states can occur due to interactions. This complex behavior cannot be or cannot sufficiently be approximated by a description having a plurality of metastable states and thus also a plurality of lifespans or of maximum decay times. There is therefore no simple exponential decay of the autofluorescence since the interactions between the molecules result in characteristic correlations in the time decay which can also go beyond the lifespan (half life). These correlations are characteristic for the totality of the molecules excited by the radiation utilized for exciting the autofluorescence since they take account of the interactions between effects. The behavior of the totality can be modeled using a time-to-time correlation of long duration which does not have any strictly exponential form.

A single molecule has a defined electron structure. Since different structures are also present in the totality of the respective molecules, the simple transition structure is lost. With two molecules, the addition of the exponential function will result in a new exponential function with a kink.

The output of energy on the drop to a lower S1 level in this respect does not take place as electromagnetic radiation (light), but the energy rather first moves at least partly to another molecule and is then output as electromagnetic radiation (autofluorescence) with modified energy since this molecule's own energy is also added. This behavior continues from molecule to molecule and the more molecules are present, the more complex this behavior is, so that subsequently no separation of the respective autofluorescence of the different molecules is possible by detection.

However, the interactions thereby also become larger and larger and can no longer be presented exponentially. An exponential behavior can still be determined on the analysis of the decay behavior of the autofluorescence. With a larger time interval away from an excitation, the profile of the exponential function no longer converges. However, precisely this non-exponential decay behavior of the autofluorescence can be taken into account with the determination of the fractal dimension $D_F$.

The determination of the fractal dimension $D_F$ can be carried out in the invention through three procedures which will be looked at in more detail in an explanatory manner in the following.

The first possibility comprises carrying out a modification to an empirically determined model using the equation $$y(t,A,B,C,\alpha,t_0) = A \cdot e^{B(|t-t_0|)^\alpha} + C \quad (3)$$

by determining the smallest error squares. $t_0$ corresponds to the time at which the maximum intensity occurs. The fractal dimension $D_F 1$ can be calculated from equation (2) via the variable a since $y(t, A, B, C, \alpha, t_0)$ can be used analog to I(t) from equation (1).

The values of the parameters A, B, C, $\alpha$, and $t_0$ can in this respect be determined fictitiously for modifying a time-dependent determination of maxima in iterative form using a modification function in accordance with Equation (3) to achieve a best possible adaptation to the experimentally determined values.

In the second possibility for calculating the fractal dimension $D_F$, the cumulative properties can be utilized. With the help of autocorrelation, relationships between the detected intensities of the autofluorescence at different points in time on the decay of the autofluorescence intensity of a measurement series can be determined. The respective then current point in time (t) can be correlated with the point in time in the range of the maximum wavelength ($t_0$) from the function y( ) in accordance with (3). In this respect, a displacement of the profile of the determined fluorescence intensities by a specific time takes place. In this respect, a difference formation can be carried out with the function profile thus displaced and the measured function value profile or the measured intensity value profile not displaced in time or time-displaced in a different manner.

The scaling law possible with cooperative fluorescence procedures can be used for the difference-autocorrelation function C(n):

$$_{7.582} C(t) \sim t^{2H} \quad (4)$$

The exponent H or the value $D_F = 2-H$ (also called a fractal dimension of the stochastic intensity fluctuations in the literature) in this respect represents the characteristic value which, as the values increase, describes an increasing collective interaction of the electrons excited by electromagnetic radiation in the blastodisk. The characteristic $D_F$ is therefore here used as a measure for distinguishing the two sexes "male" and "female".

Straight lines can be laid on the newly gained autocorrelation function which include a specific set of points in time. A new function is thus obtained whose graph is shown in FIG. 4.

A model can finally be prepared using the calculated values of the fractal dimension $D_F 1$ and $D_F 1$ using statistic methods (logistic regression and discriminant analysis) with which a classification into the classes "male" and "female" can be carried out. The discriminant analysis can be used as a control process which can confirm the results of the logistic regression. In this respect, $D_F 1$ is the value of the fractal dimension which has been determined using the first possibility while utilizing equation (3) and $D_F 2$ is the value which has been determined using the second possibility, namely the determination of the difference-autocorrelation function.

In addition, a main component analysis of the autofluorescence spectra can be carried out. This statistical process filters the essential information from the total information of a spectrum of the autofluorescence. The acquired main components can be used in a further sequence with statistical algorithms such as e.g. with a discriminant analysis for preparing a classification model.

The blastodisk should preferably be irradiated with monochromatic electromagnetic radiation. A fluorescence spectrometer can be used as a detector for the determination of the autofluorescence. The irradiation with a beam for the autofluorescence excitation should take place such that the beam is incident onto the blastodisk so that no radiation is reflected back on the same axis. The irradiation should where possible take place at an angle which differs by at least 10° from the axis aligned perpendicular to the irradiated surface of the blastodisk.

In this respect, the electromagnetic radiation used for the autofluorescence excitation can be directed to the blastodisk using an optical fiber and the electromagnetic radiation occurring as a consequence of autofluorescence can be directed to the detector using this optical fiber or a second optical fiber. In this respect, two optical fibers can be aligned at an angle obliquely inclined to one another to avoid or reduce a mutual influencing of the two radiation effects so that an optical filter in front of the detector for the wavelength of the excitation radiation can be dispensed with. On the detection of the autofluorescence intensities, however, an optical filter can be arranged in the beam path between the irradiated region of the blastodisk and the detector, with at least the electromagnetic radiation of the wavelength which is used for the autofluorescence excitation being able to be blocked by said optical filter so that radiation having this wavelength is not incident on the detector or is incident on it with an extremely small intensity. A notch filter can be used for this purpose.

Electromagnetic radiation from the wavelength range of UV radiation should be used for the autofluorescence excitation. This can be emitted from a laser light source which is preferably operated in pulsed form.

The detection should preferably be carried out with a known, and in this respect also constant, sampling rate. In this respect, the spectral analysis should in each case be carried out at respectively the same points in time. The sampling rate should lie in the range of 50 ps to 1000 ps. In this respect, the decay of the autofluorescence spectra can be detected after the switching off of the radiation source for the autofluorescence excitation with the known time intervals.

The method in accordance with the invention can be carried out in ovo without an egg having to be destroyed or without anything having to be removed from the egg for the examination. In this respect, a suitable probe can be introduced through the shell and the irradiation of the blastodisk and also the detection can be achieved through a small hole.

Each fluorescence is characteristic for a specific fluorophore. Materials, substances and molecules are also contained in the cell material of blastodisks, and can act and be used as fluorophore. They can influence one another. The different fluorescence behavior results in a complex, non-exponential decay behavior. This can be described via the fractal dimension.

The sex determination can surprisingly also be achieved using the invention in non-incubated eggs with a certainty of more than 75%, whereby the effort required for the incubation can be reduced and eggs sorted out in a sex-specific manner before the incubation can be supplied to another meaningful utilization, which is naturally particularly advantageous.

BRIEF DESCRIPTION OF THE DRAWINGS

The invention will be explained in more detail by way of example in the following.

There are shown.

DETAILED DESCRIPTION OF THE INVENTION

Figure 1:
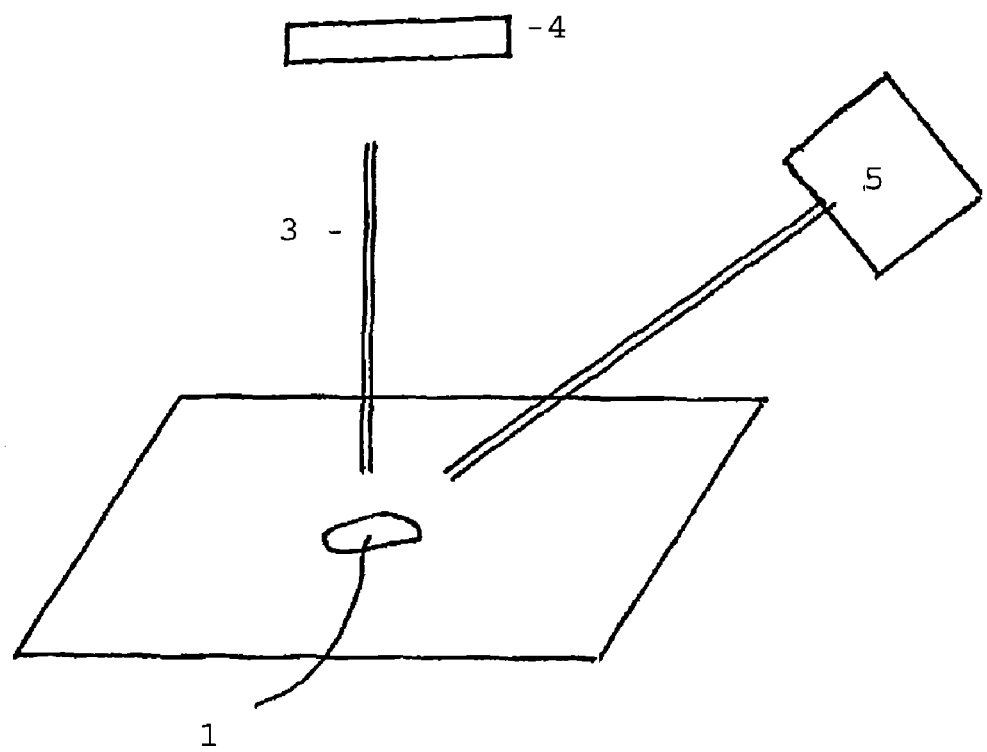
FIG. 1 in schematic form, the irradiation of a blastodisk and the detection of autofluorescence.

It is shown in FIG. 1 how laser radiation having a wavelength of 337.1 nm which has been emitted by a nitrogen laser, as the radiation source 5, for exciting autofluorescence at the blastodisk 1 is directed to a blastodisk 1 by means of the optical fiber 2. The fiber 2 is aligned at an angle in the range of 60° to 70° to the horizontal or to the plane of the blastodisk 1.

The autofluorescence radiation emitted by the blastodisk 1 can in this example be directed using the second optical fiber 3 to a detector/laser fluorescence spectrometer 4, not shown, which is suitable for spectral analysis. The optical fiber 3 is aligned perpendicular to the horizontal or to the plane of the blastodisk 1 in which it is arranged or irradiated. An influencing of the detection by the irradiation for exciting the fluorescence can thereby be avoided.

If the conducting of the radiation for the excitation and also the conducting of the autofluorescence radiation takes place via a single optical fiber or if the detection takes place directly using a suitable detector, an optical filter or a corresponding optical beam splitter can be arranged before the detector which blocks the wavelength of the electromagnetic radiation used for the excitation. In this case, a notch filter is suitable which is not transparent for electromagnetic radiation having the exciting wavelength 337.1 nm. Its blocking effect can in this respect lie in an interval ±2 nm about this wavelength.

The optical fibers 2 and 3 can in this respect be arranged with a spacing of 5 mm to 25 mm from the surface of the blastodisk 1 with their face ends facing in this direction.

If the respective radiation is conducted by means of the same optical fiber for the excitation of the autofluorescence and the detection of the respective radiation, this should be aligned as the optical fiber 2 shown in FIG. 1.

The evaluation and the determination of the fractal dimension $D_F$ which have been carried out on blastodisks from eggs of the normal domestic hen (gallus gallus domesticus) will be looked at in the following. In this respect, a nitrogen laser having a pulsed energy of 140 µJ and a pulse duration of 0.7 ns was used. It was able to be operated in pulsed manner at a frequency in the range of 2 Hz to 50 Hz. The detection took place using a fluorescence spectrometer at which a polychromator and an ICCD (intensified charge-coupled device) were present. In the detection, the autofluorescence intensities were spectrally resolved with a constant sampling rate of 250 ps in the wavelength range between a minimum of 304.6 nm and a maximum of 955.3 nm.

After the determination of the fractal dimension $D_F$ at a blastodisk of an egg, a check of the determination results took place by a determination of different sex-specific DNA portions, as was described by T. R. Tiersch in "Identification of sex in chickens by flow cytometry"; Word's Poultry Science Journal (2003); #59; p. 25-32.

Examinations were carried out on 87 blastodisks as samples.

Figure 2:
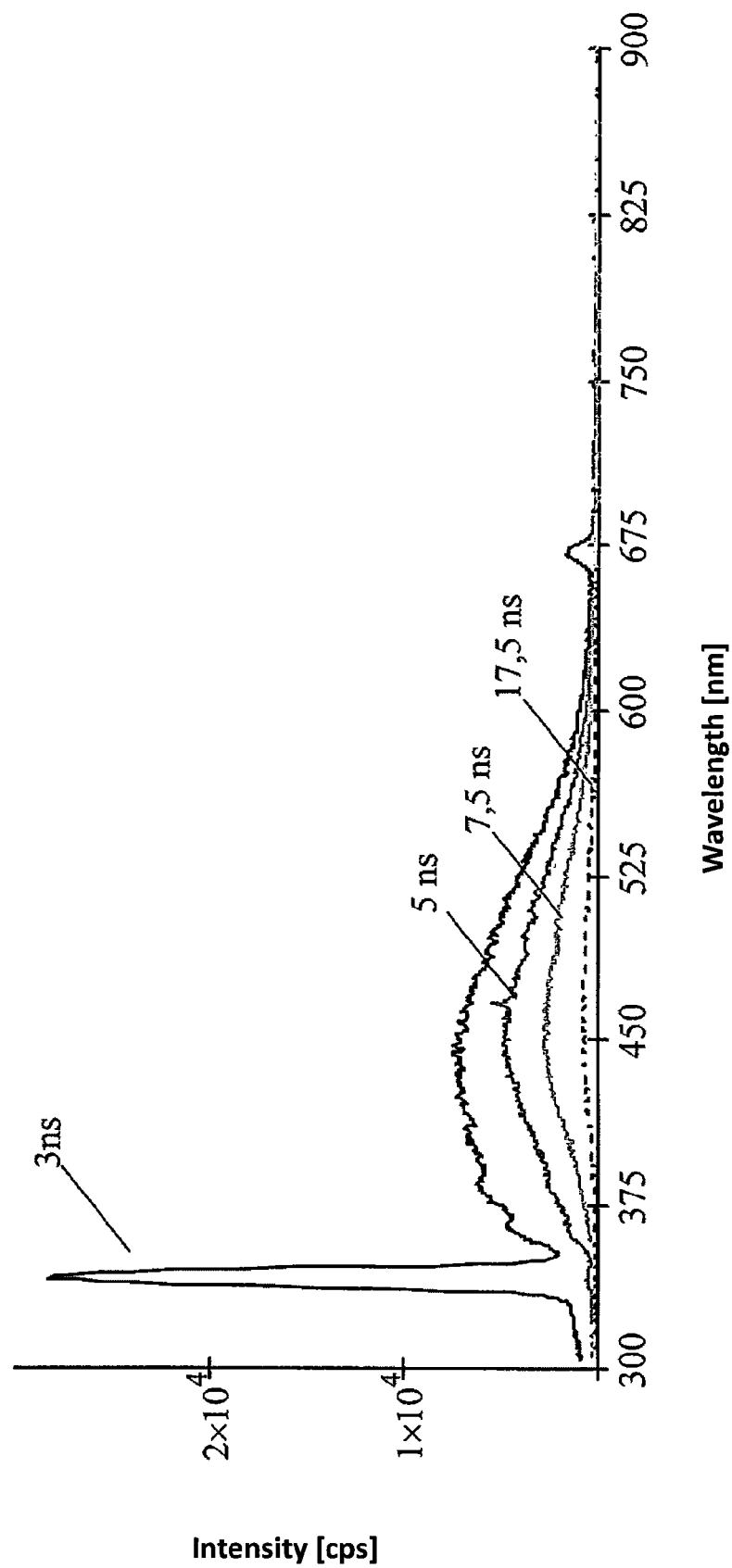
FIG. 2 a diagram of the intensities of detected autofluorescence spectra at different points in time.

In the diagram shown in FIG. 2, the four curve profiles show detected fluorescence intensities over a wavelength range from 300 nm to 900 nm at different points in time which reproduce the decay behavior of the autofluorescence intensities in spectrally resolved form. The maximum at approximately 340 nm corresponds to the wavelength of the radiation used for the autofluorescence excitation.

It becomes clear that after 17.5 ns no significant detection of autofluorescence was possible.

Figure 3:
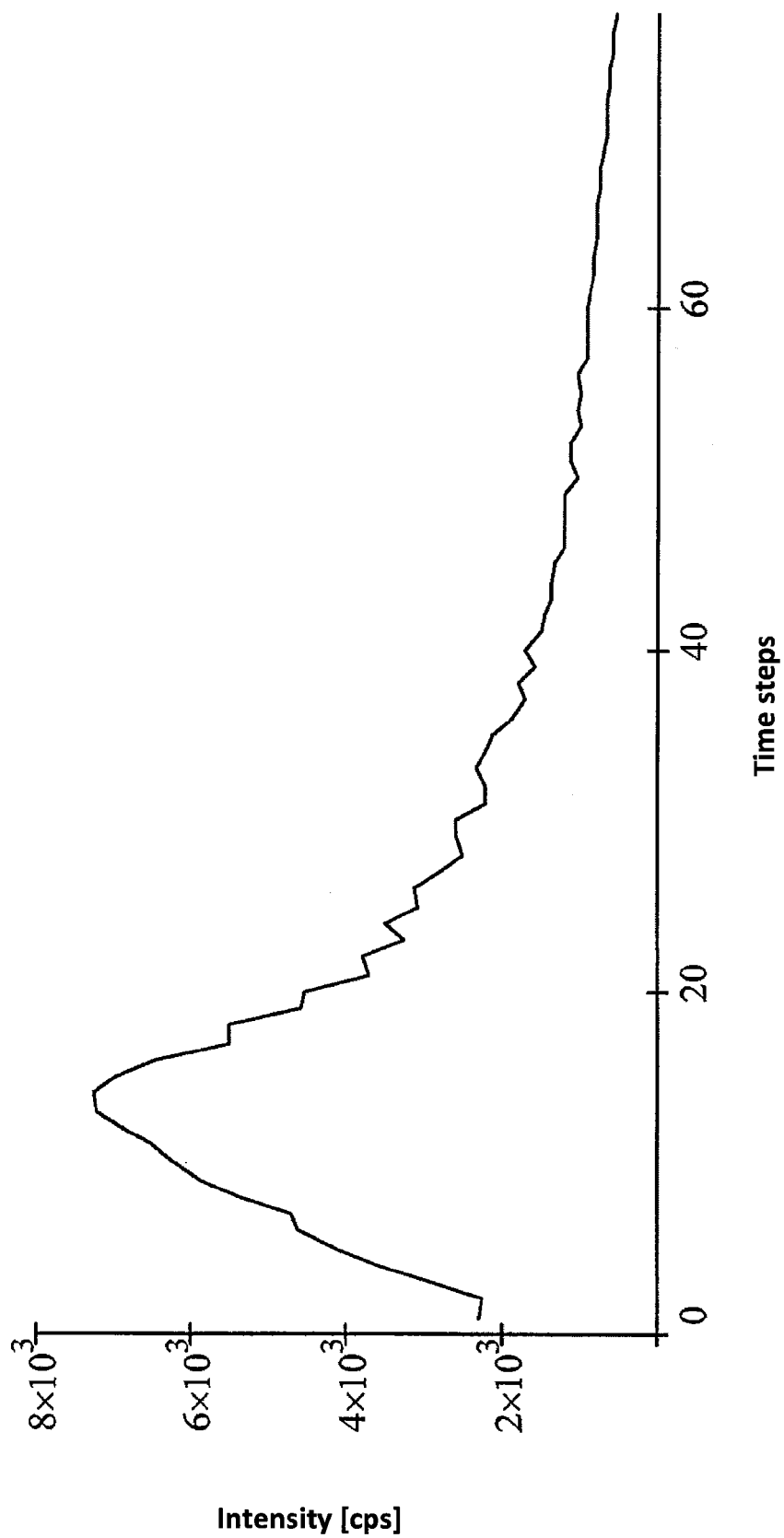
FIG. 3 the time profile of a detected autofluorescence intensity.

The time profile, that is, the decay behavior of the autofluorescence, of autofluorescence intensities is shown in FIG. 3. In this respect, thirty wavelengths were taken into account to subject the autofluorescence profile to a smoothing.

In this respect, the autofluorescence intensities of a selected wavelength range are taken into account in which the maximum autofluorescence intensity is contained.

The indication of the time steps takes account of the sampling rate of 250 ps so that 250 ps represents a time step.

Figure 4:
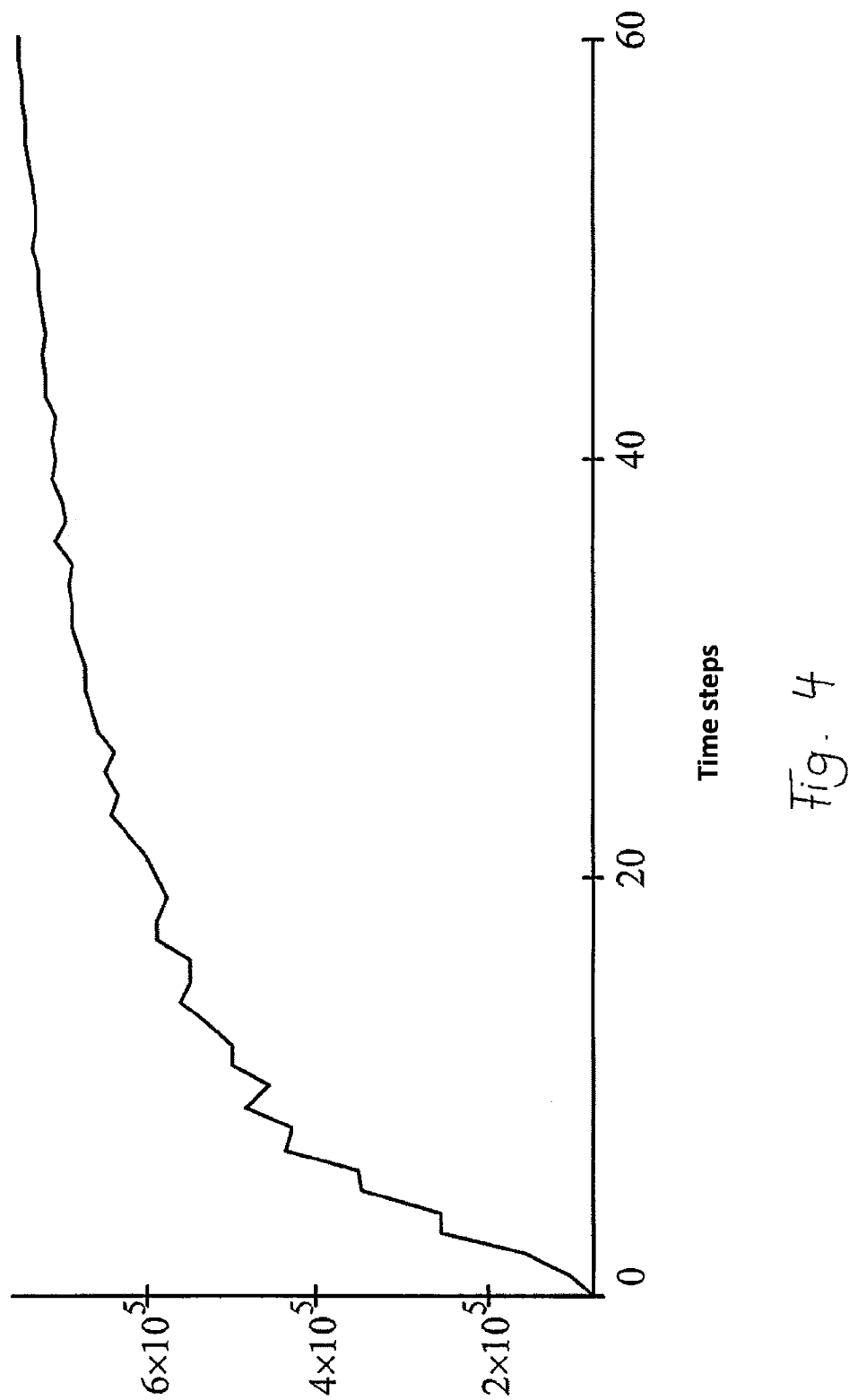
FIG. 4 the profile of a difference-autocorrelation function.

The determined difference-autocorrelation function is made visible by the diagram shown in FIG. 4. In this respect, a time displacement was carried out to mask the region in which irradiation was still being carried out for autofluorescence excitation.

Figure 5:
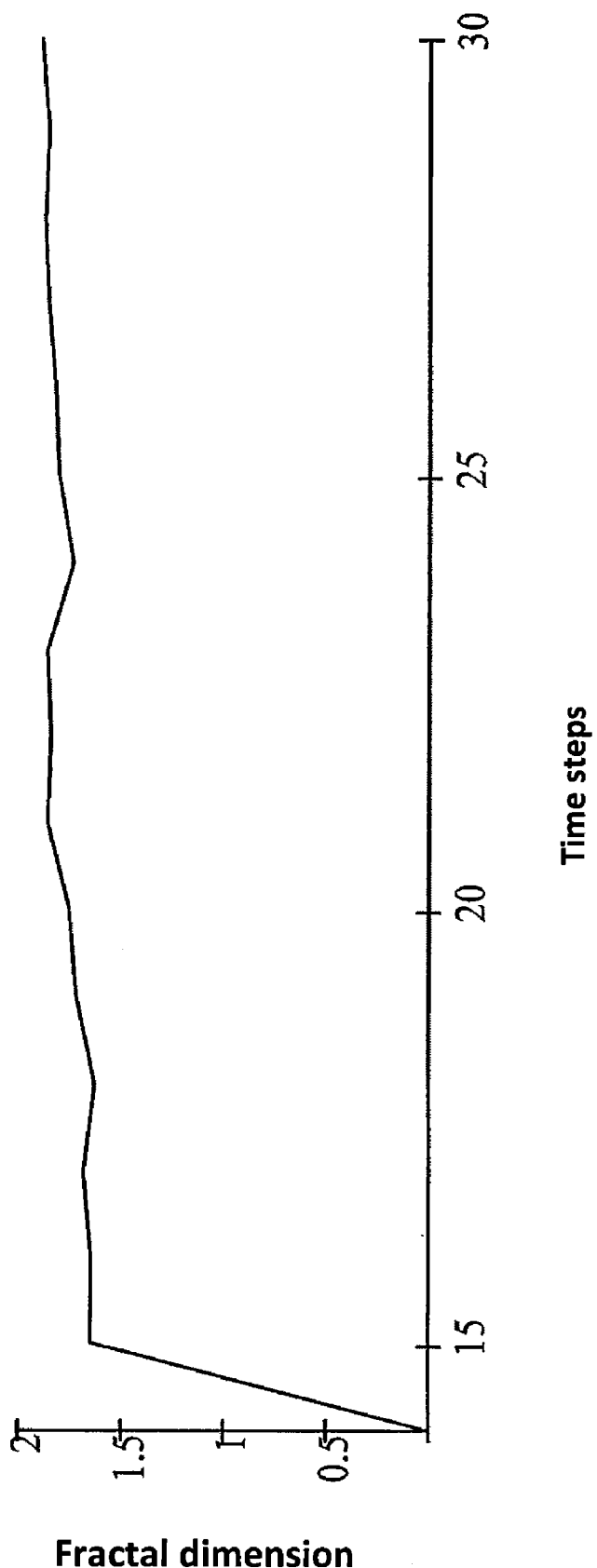
FIG. 5 the function profile of a function of the difference-autocorrelation function composed of a plurality of straight lines.

A smoothing of the difference-autocorrelation was carried out in the diagram shown in FIG. 5 in that a mean value formation took place in time intervals which resulted in time-expanded regions having the same functional gradients.

In the examinations carried out, the value 1.54 was able to be determined as a limit value for the fractal dimension $D_F 1$ via the empirical model using equation (3) in the first possibility and the value $D_F 2$ was able to be determined as 1.506 by means of the second possibility (difference-autocorrelation analysis). Accordingly, eggs with blastodisks at which the determined fractal dimension $D_F$ was in each case larger than the corresponding limit value were to be classified as female.

As already expressed in the general description, a sex determination can be carried out using one of the two explained possibilities for the determination of the fractal dimension of the temporal decay behavior of the autofluorescence intensities, that is, using $D_F 1$ or $D_F 2$. The determination security can, however, also be increased by taking account of the values of $D_F$ determined using the two possibilities. If therefore the exceeding of the limit value applies both to $D_F 1$ and $D_F 2$, the probability of the correctness of the sex-determination carried out of a female egg is higher.

What is claimed is:

1. A method for determining the sex of birds' eggs, said method comprising the steps of:
   (a) emitting electromagnetic radiation to the blastodisk of an egg by a radiation source,
   (b) switching off of the radiation source,
   (c) detecting the decay behavior of the autofluorescence intensity excited by the electromagnetic radiation with a detector at the irradiated region of the blastodisk with time resolution and spectral resolution for at least one wavelength of the autofluorescence,
   (d) calculating, using a microprocessor, fractal dimension $D_F$ using the determined measured intensity values,
   (e) comparing the value of the fractal dimension $D_F$ with a species-specific and sex-specific limit value, and
   (f) classifying the respective egg as female when the limit value is exceeded and classifying the egg as male when the limit value is not reached.

2. A method in accordance with claim 1, characterized in that the fractal dimension $D_F1$ is determined by determining the smallest error squares.

3. A method in accordance with claim 1, characterized in that the fractal dimension $D_F2$ is determined by determining the difference-autocorrelation function C(t) of the autofluorescence intensity decay behavior.

4. A method in accordance with claim 1, wherein the blastodisk is irradiated with monochromatic electromagnetic radiation and a fluorescence spectrometer is used for determining the autofluorescence, with the irradiation taking place so that the beam for the autofluorescence excitation is incident onto the blastodisk so that no radiation is reflected on the same axis.

5. A method in accordance with claim 1, wherein the detection is carried out with a known, constant sampling rate.

6. A method in accordance with claim 5, wherein the detection is carried out with a constant sampling rate in the range of 50 ps to 1000 ps.

7. A method in accordance with claim 1, wherein electromagnetic radiation from the wavelength range of UV radiation is used for the fluorescence excitation.

8. A method in accordance with claim 1, wherein the electromagnetic radiation used for the fluorescence excitation is directed to the blastodisk by means of a first optical fiber and the electromagnetic radiation occurring as a consequence of autofluorescence is directed to the detector via a second optical fiber and in this respect the two optical fibers are aligned at an obliquely inclined angle with respect to one another.

9. A method in accordance with claim 1, wherein the determination is carried out in ovo.

* * * * *

UNITED STATES PATENT AND TRADEMARK OFFICE
CERTIFICATE OF CORRECTION

| | |
|---|---|
| PATENT NO. | : 8,364,247 B2 |
| APPLICATION NO. | : 12/960678 |
| DATED | : January 29, 2013 |
| INVENTOR(S) | : Joerg Opitz et al. |

It is certified that error appears in the above-identified patent and that said Letters Patent is hereby corrected as shown below:

Title Page, Item (75) Inventors: Bjoern Fischer, replace "Limbach-Oberfohna" with --Limbach-Oberfrohna--;

Item (73) Assignee: Replace "Fraunhofer-Gesellschaft zur Foerderung der Angwandten Forschung E.V." with --Fraunhofer-Gesellschaft zur Foerderung der Angewandten Forschung E.V.--.

Signed and Sealed this
Ninth Day of April, 2013

Teresa Stanek Rea
*Acting Director of the United States Patent and Trademark Office*